United States Patent [19]

Mercier et al.

[11] Patent Number: 5,064,934
[45] Date of Patent: Nov. 12, 1991

[54] THERMOSETTING POLYIMIDE SCHIFF BASE RESINS, THEIR PREPARATION AND THEIR APPLICATIONS

[75] Inventors: Regis Mercier, Vimy; Thierry Pascal, Feyzin; Bernard Sillion, Lyon, all of France

[73] Assignee: Centre d'Etude des Materiaux Organiques pour Technologies Avancees, Vernaison, France

[21] Appl. No.: 502,275

[22] Filed: Apr. 2, 1990

[30] Foreign Application Priority Data

Mar. 31, 1989 [FR] France .................. 89 04391

[51] Int. Cl.$^5$ .................. C08G 12/06
[52] U.S. Cl. .................. 528/220; 528/226; 528/228; 528/229; 528/230; 528/244; 528/246; 528/247; 528/248; 528/266; 528/353
[58] Field of Search .............. 528/220, 226, 228, 229, 528/230, 244, 246, 247, 248, 266, 353

[56] References Cited

U.S. PATENT DOCUMENTS 4,645,821 2/1987 Malinge et al. .................. 528/331
4,987,218 1/1991 Malinge et al. .................. 528/353

*Primary Examiner*—John Kight, III.
*Assistant Examiner*—Sam, A. Acquah

*Attorney, Agent, or Firm*—Millen, White & Zelano

[57] ABSTRACT

Thermosetting Schiff base resins, their preparation and their applications are described.

These thermosetting Schiff base resins can be defined as responding to the general formula:

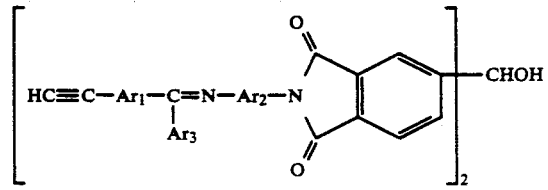

Radicals $Ar_1$, $Ar_2$ and $Ar_3$ are chosen so that the softening temperature of the resins is less than about 150° C.

The resins can be prepared by direct condensation of an ethynyl benzaldehyde or acetophenone on a telechelic diamine oligomer obtained by reaction of a diamine containing flexibilizing groups on a derivative of benzhydrol tetracarboxylic acid. These Schiff base resins can be used by bulk thermal polymerization particularly to prepare adhesives or composite matrices.

10 Claims, No Drawings

THERMOSETTING POLYIMIDE SCHIFF BASE RESINS, THEIR PREPARATION AND THEIR APPLICATIONS

This invention has as its object organic resins resistant to temperature and bulk polymerizing without releasing volatile products.

The thermostable structures, their chemistry and their properties now are well described (P. E. Cassidy, "Thermally Stable Polymers," Marcel Dekker, 1980, and J. P. Critchley, G. J. Knight, W. W. Wright, "Heat Resistant Polymers," Plenum Press 1983). These materials find applications particularly in industrial fields such as electrical engineering, electronics, microelectronics or separation techniques. Thermoplastic thermostable polymers, whose aromatic or heterocyclic main chain is made more flexible by bonds of ether, sulfur, perfluoroisopropylidene or others, are distinguished. These polymers can be used from solutions or else in bulk above the glass transition temperature or the melting point for their uses, for example, as adhesives or in composite materials. Under these conditions, it is necessary to apply strong pressures and the heat resistance of the material is limited by the glass or crystalline transitions.

The second class of polymers sought for the structural applications is that of the thermosetting polymers. Some are linear. They are used in the form of operational oligomers of low molecular weight, and the polycondensation continues under the conditions of the use. This is the case of polybenzhydrolimides described particularly in French patent FR. A-1 601 091. The drawback of these resins is that it is necessary to use them in polar aprotic solvents with a high boiling-point.

PMR ("polymerization of monomeric reactants") resins, particularly those marketed under the name of PMR 15, are mixtures obtained by condensation between the methyl diester of the benzophenonetetracarboxylic acid, the methyl monoester of the nadic acid and an aromatic diamine such as, for example, diamino-4,4'-diphenylmethane. The proportions of reagents are calculated so that the theoretical molecular weight of the product is about 1500 and all the molecules are terminated by nadic groups at each end. At the time of use, the condensation and the imidation reactions occur, then, at a higher temperature (about 270° C.), the polymerization of the reactive ends occurs, causing the crosslinking of the system (T. T. Serafini, P. Delvigs, G. R. Lightsey, J. Appl. Polym. Sci., 16, 905, 1972).

These reagents are unstable at ambient temperature and delicate to use. This evolution toward the thermostable thermosetting systems therefore poses at least two significant problems: the selection of the linkage between the reactive functions and the selection of two terminal reactive functions. The linkage between the reactive functions should not release volatile products during use and consequently should be totally condensed and/or cyclized. Further, the nature of this linkage will set the softening point of the resin before the reaction, but also the glass transition of the network after crosslinking.

With regard to the two reactive functions, three large families are distinguished: the maleimide, nadimide and acetylene functions.

The acetylene functions polymerize at a low temperature: very slowly from 150° C. and quickly between 200° and 250° C.

The polymerization of the maleimides depends considerably on the environment, and three types of polycondensation are identified: nucleophilic addition polymerization (Michael addition), free-radical polymerization, anionic polymerization. It is difficult to control the use reactions, and if the polycondensation by diamine addition is considered, the presence of free amine in the resin makes this type of material subject to the legislation on toxicity. The polymerization of nadic groups makes a retro Diels-Alder reaction occur which frees a maleimide function and a cyclopentadiene molecule. The use of this type of resin therefore necessitates a delicate selection of temperature and pressure so that the volatile diene is incorporated in the material by polymerization.

It therefore is not surprising to see that, for new thermostable resins, the selection of the reactive function is oriented to the ethynylized resins despite a certain synthesis difficulty in introducing the acetylene function into the molecule. The resin Thermid 600 (marketed by National Starch) is an example of an oligoimide (or isoimide) terminated by an ethynyl function at each end. However, it should be noted that these resins melt at a temperature higher than the beginning temperature of polymerization of the acetylenes, which is a drawback, because it will be difficult to moisten the reinforcement well if a molten state is not passed through.

It is the same for most quinoxaline resins terminated by the acetylene groups studied by NASA and called ATQ (U.S. patent application. 518 897 or R. F. Kovar, G. F. L. Ehlers, F. E. Arnold, Polym. Prep. Am. Chem. Soc. Div. Polym. Chem. 16 (2) 246 1975).

This is generally the drawback of most of the heterocyclic resins which are intrinsically rigid. Attempts have been made to get around this difficulty by abandoning the heterocyclic linkage in favor of the ether sulfone type linkage. The resins obtained, called ATS, make possible a fusible stage before the crosslinking of the terminal acetylene groups (U.S. Pat. No. 4,131,625 and R. F. Kovar, G. F. L. Ehlers, F. E. Arnold, J. Polym. Sci., Polym. Chem. Ed. 15, 1981, 1977). On the other hand, the glass transition temperature of the crosslinked network is often low.

In a general way, the Schiff base polymers of aromatic type are presented as thermostable but insoluble structures (G. F. D'Alelio, R. K. Schoenig, J. Macromol. Sci. C3 (1) 105-234 (1969)).

Recently, R. Rossi, S. Fenelli and E. Hartmann published in the ANTEC Congress 1988 monomers and oligomers terminated by acetylene functions and whose linkages are made by Schiff bases. These products are good insulators after crosslinking, but they become conductors on the order of $10^{-1}$ to $10^{-2}$ S/cm by heating to 800° C.

It now has been discovered that some benzhydrolimide oligomers terminated by acetylenes bonded to the imides by Schiff base structures make possible the preparation of soluble acetylene resins exhibiting sufficiently low softening temperatures so that the polymerization of the acetylene begins in the molten state. Further, these resins, after crosslinking, have a sufficiently high glass transition for high temperature applications. The object of this invention is precisely to describe these resins, their process of production and their bulk polymerization reaction.

In a general manner, the resins of the invention can be defined in that they respond to the general formula

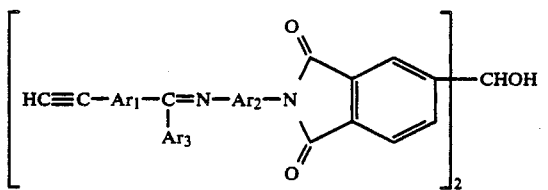

in which Ar$_1$ is an unsaturated heterocyclic radical or a divalent mono- or poly-cyclic aromatic radical containing from 6 to 20 carbon atoms; when Ar$_1$ comprises several aromatic rings, the latter can be joined or bonded to one another by a single connection or by an atom or a divalent group such as:

—CHOH—; —CO; —CH$_2$—; —S—;

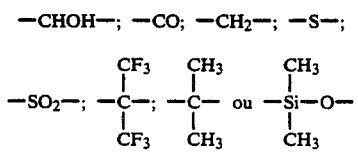

The aromatic ring or rings of radical Ar$_1$ can be nonsubstituted or substituted by at least one alkyl group of 1 to 3 carbon atoms, preferably by a methyl group.

Of the Ar$_1$ radicals preferably usable in the framework of the invention, the ortho-, meta- and para-phenylene, naphthylene 1.5, −1.6 and −2.6 radicals will be cited.

Ar$_2$ can be a divalent carbocyclic or heterocyclic aromatic radical containing from 12 to 30 carbon atoms and consisting of at least two single aromatic rings, joined or bonded two by two by an atom or a divalent group, for example, a divalent aliphatic or perfluoroaliphatic group or a heteroatom or a divalent heteroatomic group, such as

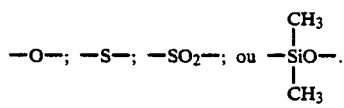

In the framework of the invention, m.phenylene, methylene biphenylene, oxybiphenylene radicals can advantageously be cited.

Ar$_2$ also can be an aliphatic divalent radical consisting of linear or branched linkages and/or linkages containing siloxane type sequences or heteroatomic bonds.

In the framework of the invention, the tri-, tetra-, penta-, hexa-, hepta-, octa-, nona-, deca-, undeca- and dodeca-methylene radicals can be cited. The trimethyl-2,2,4-hexamethylene radical, and the alpha-,omega-trimethylene polyoxyethylene, polyoxypropylene and polyoxytetramethylene radicals also can be cited. The alpha-,omega-trimethylene polysiloxanylene radicals also can be cited.

Ar$_3$ is a hydrogen atom or a mono- or poly-cyclic, aliphatic or aromatic, monovalent radical, containing from 6 to 20 carbon atoms. When Ar$_3$ comprises several aromatic rings, the latter can be joined or bonded to one another by a single bond or by an atom or a divalent group, such as:

—CHOH—; —CO; —CH$_2$—; —S—;

-continued

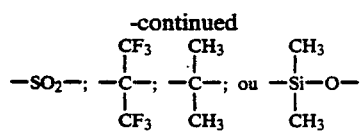

The aromatic ring or rings of the Ar$_3$ radical can be nonsubstituted or substituted by alkyl groups of 1 to 3 carbon atoms, preferably by a methyl group.

The Ar$_3$ radicals preferably considered in the framework of the invention are hydrogen or the methyl or phenyl radicals.

The selection of radicals Ar$_1$, Ar$_2$ and Ar$_3$ is made so that the softening temperature of the resin is less than 150° C.

The resins of the invention can be prepared by using various reaction sequences. However, the following structural formula is preferably used: an aldehyde or a ketone containing the acetylene pattern is prepared according to equation 1:

in which Ar$_1$ and Ar$_3$ are defined as above, and X is a halogen atom, preferably bromine or iodine.

This ethynylation reaction can be performed, for example, according to the process described by W. B. Austin, N. Bilow, W. J. Kelleghan and K. S. Y. Lan, J. Org. Chem., 46, 2280–2286 (1981).

The ethynyl aldehyde or the ethynyl ketone then is condensed on a diamine at the rate of about two equivalents of aldehyde or ketone per one equivalent of amine according to equation 2:

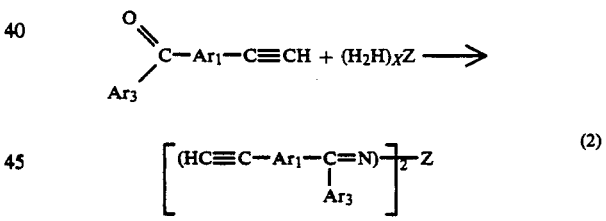

in which 2 is the divalent radical of general formula

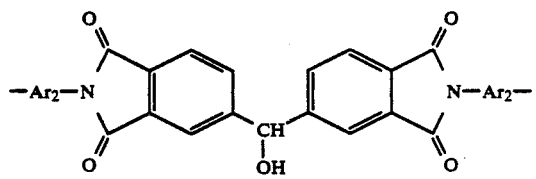

where Ar$_2$ is defined as above.

This latter reaction can be performed in an alcoholic, chlorinated or aromatic solvent, in THF, dioxane, ethyl diglyme or ethyl acetate, preferably in the presence of acid.

According to another method, an ethynyl aldehyde or an ethynyl ketone and the benzhydrol tetracarboxylic anhydride can be made to react simultaneously with a diamine of general formula NH$_2$—Ar$_2$—NH$_2$, where Ar$_2$ is defined as above.

The acetylene benzhydrolimide resins containing the Schiff base patterns, object of the invention, are in the form of amorphous materials whose softening temperature is less than 150° C. This feature makes possible a polymerization of the acetylenes in the condensed state in molten form making possible a good moistening of the surfaces, a necessary condition for the resins to exhibit good adhesive properties.

The polymerization of these resins is performed by simple heating at a temperature between 150° C. and 250° C.

After polymerization, the resins lose only 1% of their initial weight at a temperature higher than 400° C. under air. For the base resins melting below 150° C., the glass transition temperature after polymerization determined by thermomechanical analysis is higher than 280° C., which makes possible a high temperature application without altering the mechanical properties. These resins find applications in electronics for making conducting or insulating thermostable glues and in the field of structural materials to prepare composite matrices.

The following examples illustrate the invention without limiting its scope.

EXAMPLE 1

Synthesis of bis-N,N′((((N-(ethynyl)-4 benzylidene) amino-3 phenoxy)-2 pyridine)6 oxy-3 phenyl) benzhydrolimide. (Resin A)

Method 1

0.2 mole of ethynyl-4 benzaldehyde and 0.1 mole of benzhydrol tetracarboxylic acid anhydride are poured into a solution of 0.2 mole of bis((amino-3)phenoxy)-2,6 pyridine and 160 cc of diglyme maintained at 5° C. The reactional environment is allowed to develop for 4 hours at this temperature. Then, it gradually rises to 150° C. and the reaction is allowed to turn for 5 hours. The product obtained is an amorphous solid whose Tg is at 95° C. (measured by DSC).

Method 2

0.2 mole of bis((amino-3)phenoxy)-2,6 pyridine, 0.1 mole of the methyl hemiester of benzhydrol tetracarboxylic acid in 160 cc of diglyme are maintained at 140° C. for two hours. The solution then is cooled to ambient temperature to add 0.2 mole of ethynyl-4 benzaldehyde to the solution. The solution then is allowed to develop for 8 hours.

EXAMPLE 2

Thermostability of the acetylene resin of example 1

The resin treated according to the baking cycle under air: 60 minutes at 140° C., 75 minutes at 200° C. and 240 minutes at 280° C., undergoes a thermodegradation above 390° C.

The table below consolidates the results obtained by thermogravimetry under air at 5° C. per minute.

| Weight loss | 1% | 5% | 10% |
| --- | --- | --- | --- |
| Compound A | 413° C. | 470° C. | 505° C. |

EXAMPLE 3

The softening temperature of resin A as well as the glass transition temperature of the polymerized resin (baking cycle according to example 2) have been determined.

The values are indicated in the table below.

| Resins | Tr (°C.) (*) | Tv (°C.) (**) |
| --- | --- | --- |
| Resin A | 95 | 280 |

(*) Tr Softening temperature
(**) Tv Glass transition temperature

We claim:

1. Thermosetting resin characterized in that it responds to the general formula

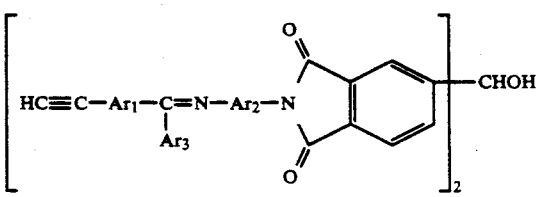

in which $Ar_1$ represents a divalent unsaturated heterocyclic radical or a divalent mono- or poly-cyclic aromatic radical containing from 6 to 20 carbon atoms; $Ar_2$ represents a divalent aromatic radical of 12 to 30 carbon atoms or a divalent aliphatic radical; and $Ar_3$ represents a hydrogen atom or a divalent aliphatic radical or a monovalent mono- or poly-cyclic aromatic radical containing from 6 to 20 carbon atoms; and its softening temperature is less than 150° C.

2. Thermosetting resin according to claim 1, wherein $Ar_1$ represents an ortho-, meta- or para-phenylene radical or a naphthylene-1,5, -1,6 or -2,6 radical.

3. Thermosetting resin according claim 1, wherein the $Ar_2$ radical is chosen from the methylene biphenylene, oxybiphenylene radicals and from the tri-, tetra-, penta-, hexa-, hepta-, octa-, nona-, deca-, undeca-, and dodeca-methylene radicals, the trimethyl-2,2,4 hexamethylene radical, the alpha-omega-trimethylene polyoxyethylene, polyoxypropylene and polyoxytetramethylene radicals, and the alpha,omega-trimethylene polysiloxanylene radicals.

4. Thermosetting resin according to claim 1, wherein $Ar_3$ represents hydrogen, a methyl radical or a phenyl radical.

5. Process of preparing a thermosetting resin according to claim 1, wherein it comprises:

a) the ethynylation of an aldehyde or a ketone of general formula

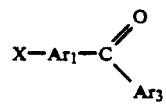

into an ethynyl aldehyde or an ethynyl ketone of general formula

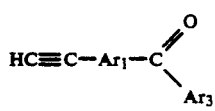

$Ar_1$ and $Ar_3$ being defined in the same manner as in one of claims 1 to 4 and X representing a halogen atom; and b) the condensation of the ethynyl aldehyde or the ethynyl ketone formed in stage (a) with a diamine of general formula $NH_2-Z-NH_2$, in which Z represents a divalent radical of general formula

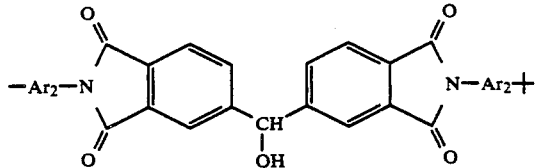

where $Ar_2$ is defined in the same manner as in one of claims 1 to 4.

6. Process of preparing a thermosetting resin according to claim 1, wherein it comprises:

a) the ethynylation of an aldehyde or a ketone of general formula

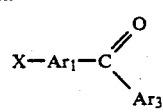

into an ethynyl aldehyde or an ethynyl ketone of general formula:

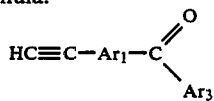

$Ar_1$ and $Ar_3$ being defined in the same manner as in one of claims 1 to 4 and X representing a halogen atom; and b) the simultaneous reaction of the ethynyl aldehyde or the ethynyl ketone formed in stage (a) and the benzhydrol tetracarboxylic anhydride with at least one diamine of general formula $NH_2-Ar_2-NH_2$ where $Ar_2$ is defined in the same manner as in one of claims 1 to 4.

7. A process of a thermosetting resin according to claim 1, in which said resin is subjected to a thermal polymerization.

8. Use according to claim 7, wherein said resin is heated to a temperature from 150° to 250° C.

9. Use according to claim 7, wherein a thermostable glue is produced.

10. Use according to claim 7, wherein a composite matrix is produced.

11. In a process for the preparation of a polymer, said process comprising subjecting a thermosetting resin to thermal polymerization, the improvement wherein the resin is one of claim 1.

12. In a process for the preparation of a thermostable adhesive or a composite matrix, said process comprising subjecting a thermosetting resin to thermal polymerization, the improvement wherein the resin is one of claim 1.

* * * * *